United States Patent [19]
Clift, Jr. et al.

[11] Patent Number: 5,326,364
[45] Date of Patent: Jul. 5, 1994

[54] TRAPEZIAL IMPLANT

[75] Inventors: Joseph S. Clift, Jr., Memphis; Kelly C. Richelsoph, Cordova, both of Tenn.; James W. Strickland, Zionsville, Ind.

[73] Assignee: Wright Medical Technology, Inc., Arlington, Tenn.

[21] Appl. No.: 991,609

[22] Filed: Dec. 16, 1992

[51] Int. Cl.⁵ .................................. A61F 2/42
[52] U.S. Cl. .......................... 623/21; 623/18; 623/20; 606/69
[58] Field of Search .............. 623/18, 19, 20, 21, 623/22; 606/76, 69, 70

[56] References Cited

U.S. PATENT DOCUMENTS

| | | | |
|---|---|---|---|
| 4,085,466 | 4/1978 | Goodfellow et al. | 623/20 |
| 4,164,793 | 8/1979 | Swanson | 623/21 |
| 4,242,759 | 1/1981 | White | 623/21 |
| 4,301,552 | 11/1981 | London | 623/18 |
| 4,778,473 | 10/1988 | Matthews et al. | 623/20 |
| 4,936,854 | 6/1990 | Swanson | 623/21 |
| 4,936,860 | 6/1990 | Swanson | 623/21 |
| 4,955,915 | 9/1990 | Swanson | 623/21 |
| 4,969,908 | 11/1990 | Swanson | 623/21 |

Primary Examiner—Paul Prebilic

[57] ABSTRACT

A trapezial implant is provided for attachment to the trapezium of a hand. The implant includes a base member fabricated from an inelastic material such a medical grade metal or ceramic. The base member includes a generally planar proximal attachment surface from which extend two pentihedral-shaped spikes. The base member also includes a distal articular surface having a non-symmetrical, complex curvature. The implant is retained in place on the trapezium under compression of the first metacarpal.

2 Claims, 3 Drawing Sheets

TRAPEZIAL IMPLANT

TECHNICAL FIELD

The subject invention relates generally to a prosthetic bone implant and more particularly to a trapezial resurfacing prosthesis.

BACKGROUND ART

Conditions such as osteoarthritis, cancer or trauma may cause degeneration of the articular surfaces between the trapezium and the first metacarpal in a hand causing the patient discomfort and sometimes severe pain during thumb circumduction.

Various total replacement prosthesis have been proposed for bones in the human wrist. For example, U.S. Pat. No. 4,936,860 to Swanson, issued Jun. 26, 1990, discloses a metallic total scaphoid replacement implant. Also, U.S. Pat. Nos. 4,955,915 and 4,969,908 both to Swanson, issued Sept. 11, 1990 and Nov. 13, 1990, respectively, disclose total lunate replacement implants. Although not directed to a carpal bone implant, U.S. Pat. No. 4,936,854 to Swanson, issued Jun. 26, 1990, discloses an implant anchored in the radius and having a cupped, or dished, surface for stabilizing the proximal carpal row and preventing ulnar migration thereof.

As an alternative to total carpal bone replacement, it is well known in the art to resurface the distal surface of the trapezium with a prosthetic implant. For example, the Silastic ® Trapezial Implant H.P., manufactured by Dow Corning Wright Corp. 5667 Airline Road, Arlington, Tenn. 38002, is made from medical grade silicone rubber elastomer for use as an interpositional spacer between the trapezium and the first metacarpal joint of the thumb. The implant is provided with a short cylindrical stem extending from its proximal surface which fits into a cavity prepared in the trapezium. The head, or distal articular surface, of the implant is thin and dome-shaped.

One of the goals of implant design is to minimize the production of wear debris particles. Wear particles can never be completely eliminated with presently available implant materials because all moving parts, e.g., implants that articulate against bone, wear to some degree. It is generally believed by some that elastomers generate wear particles at a more accelerated rate than inelastic materials. However, because the distal articular surface of the aforementioned Silastic ® Trapezial Implant H.P. is domed, i.e., not anatomically representative of a natural trapezium, that implant must be manufactured from an elastomer due which has the ability to deform so as to better articulate with existing joint anatomy.

SUMMARY OF THE INVENTION AND ADVANTAGES

The subject invention provides an implant for attachment to the distal surface of a prepared trapezium. The trapezial implant comprises a base member having a proximal attachment surface and a distal articular surface, and anchor means extending from the proximal attachment surface for anchoring or fixing the base member to the prepared surface of the trapezium. The distal articular surface includes a convex medial portion, a convex lateral portion, and a concave central portion between the medial and lateral portions defining a distinctive and complex surface curvature for providing stable support to an adjacent first metacarpal through the entire arc of thumb circumduction. That is, the complex surface curvature provides improved articulation with the adjacent first metacarpal because its configuration closely replicates the normal human distal trapezium articular surface. In other words, the distal articular surface mimics the natural joint anatomy.

The specific shape of the distal articular surface provides improved articulation between the distal articular surface of the implant and the first metacarpal thereby reducing the production of wear particles due to attrition. Further, because the distal articular surface is formed having medial and lateral convex portions and a central concave portion, the base member can be fabricated from an in-elastic, less abradable materials than the prior art elastomers. Thus, the subject invention overcomes a need inherent in the prior art domed trapezial implants fabricated from silicone elastomers.

BRIEF DESCRIPTION OF THE DRAWINGS

Other advantages of the present invention will be readily appreciated as the same becomes better understood by reference to the following Detailed Description when considered in connection with the accompanying Drawings wherein.

DETAILED DESCRIPTION

Figure 1:
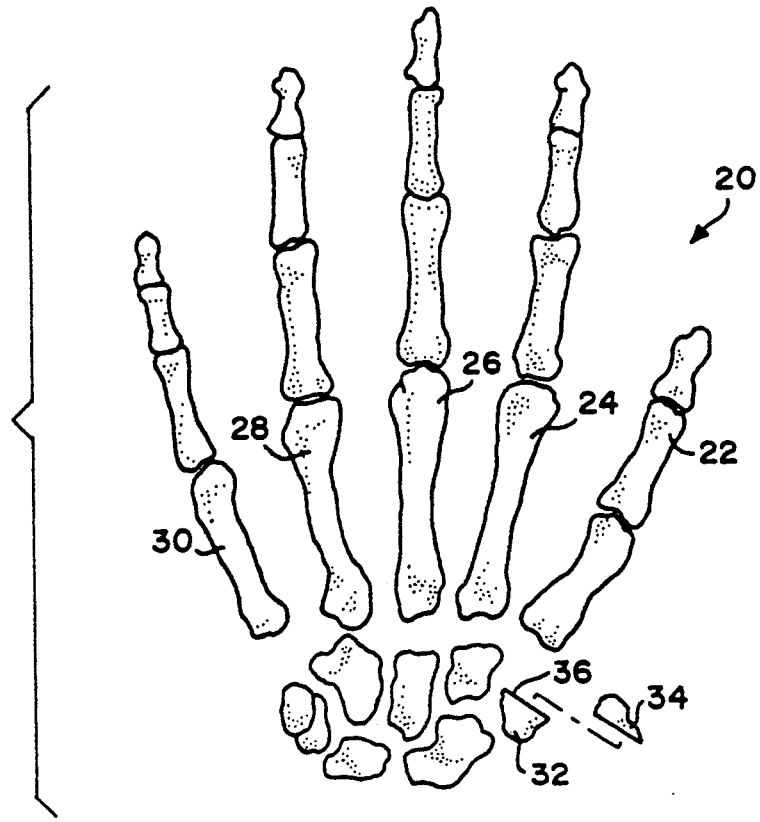
FIG. 1 is a simplified dorsal view of a human skeletal hand showing the distal articular surface of the trapezium excised.
Figure 2:
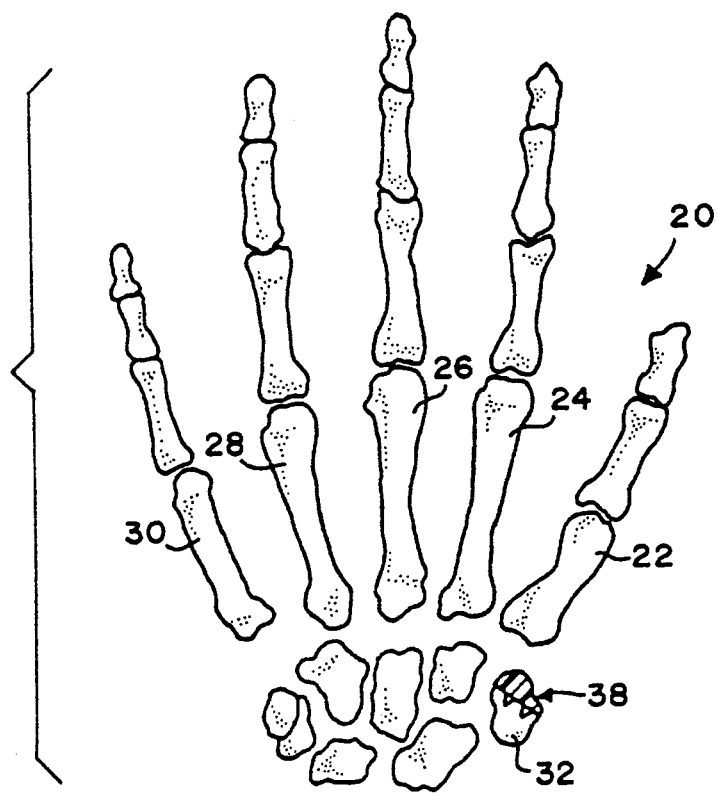
FIG. 2 is a view as in FIG. 1 showing the subject trapezial implant operatively positioned on the trapezium.

Referring to the Figures, wherein like numerals indicate like and corresponding parts throughout the several views, a human hand skeleton is generally shown at 20 in FIGS. 1 and 2. The hand 20 includes first 22, second 24, third 26, fourth 28, and fifth 30 metacarpals. The first metacarpal 22 is located medial relative to the fifth metacarpal 30. The hand 20 has a carpus comprising eight bones, including the trapezium 32.

Some physical conditions, e.g., arthritis, cancer, trauma, etc., necessitate arthoplastic surgery to prosthetically improve the articular surfaces between the first metacarpal 22 and the trapezium 32. The prior art has taught both total replacement as well as resurfacing of the trapezium 32. In many instances, resurfacing is preferred and more conservative of bone than total excision of the trapezium 32.

The trapezium 32 is prepared for the hemiarthroplasty as follows. The carpometacarpal joint of the thumb is exposed through a transverse or curved longitudinal incision. The superficial sensor branch of the radial nerve is identified and protected. The abductor pollices longus tendon is detached at its insertion and the extensor pollices brevis tendon is retracted. The joint capsule is opened and preserved. The marginal osteophytes at the base of the metacarpal 22 and trapezium 32 are removed with a rongeur. Distal traction of the thumb allows the joint surfaces to be well-visualized. With either an osteotome or power sagittal saw, the saddle 34 of the trapezium 32 is converted to a flat surface 36, and the medial osteophyte is removed. Excision of this medial spur permits further debridement of the capsule and reduction of the subluxed metacarpal. It is imperative that all bony obstruction to metacarpal reduction be removed. FIG. 1 illustrates the distal articular portion or saddle 34 resected from the trapezium 32, such as by conventional procedures as described above. This saddle 34 is excised to form a stable, transverse interface 36 to eliminate shear stresses.

In place of the excised saddle 34, a trapezial implant, generally indicated at 38 in FIGS. 2–5, is attached to the trapezial bone 32, as shown in FIG. 2. The implant 38 includes a base member 40 preferably fabricated from an inelastic and abrasion resistant material, such as commercially pure titanium, other medical grade metals or alloys, or alumina, zirconia or silica ceramics. The base member 40 includes a generally planar proximal attachment surface 42 structured to engage in surface-to-surface contact with the interface 36 of the prepared trapezium 32. The base member 40 further includes a distal articular surface 44 constructed and adapted to mimic the natural geometry of the saddle 34.

In addition to the materials listed above, the implant 38 can be fabricated from zirconium with a coating of zirconium oxide for improved abrasion resistance. The implant 38 can also be formed of zirconium alloys including titanium, niobium, hafnium and other metals known to form stable alloys with zirconium.

Figure 3:
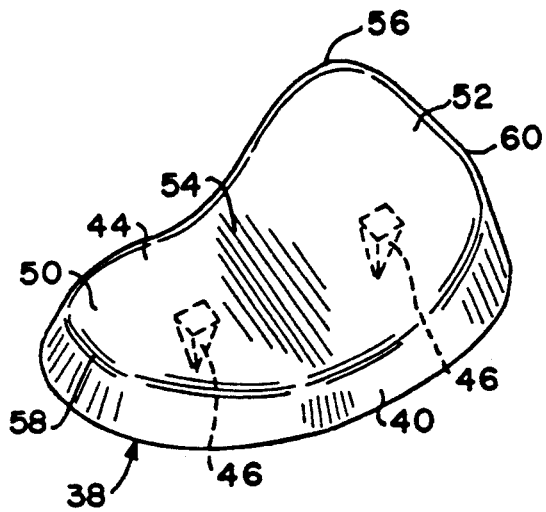
FIG. 3 is a perspective view of a trapezial implant according to the subject invention.
Figure 4:
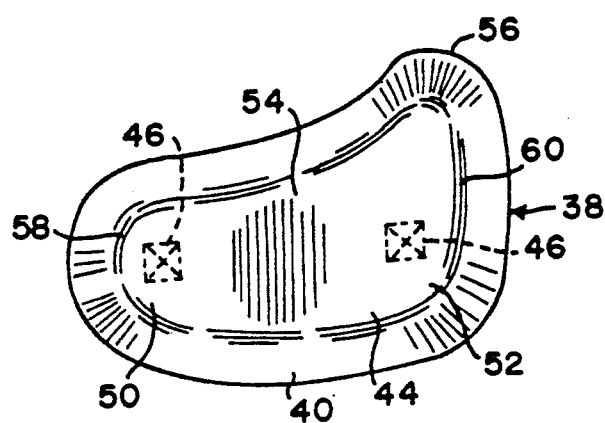
FIG. 4 is a plan view of the implant as in FIG. 3.
Figure 5:
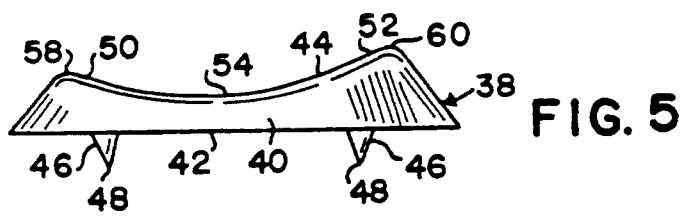
FIG. 5 is a front elevational view of the trapezial implant as in FIG. 4.

An anchor means extends from the proximal attachment surface 42 of the base member 40 for anchoring the base member 40 to the trapezium 32. As illustrated in FIGS. 3–5, the anchor means preferably includes at least a pair of spaced posts 46 extending perpendicularly from the proximal attachment surface 42. Each of the posts 46 taper proximally to a pointed tip 48. As shown in FIGS. 3 and 4, the posts 46 are preferably pentahedral, or pyramidal, but also may be conical, tetrahedral or other simple pointed shape, and have a length substantially less than prior art cylindrical stems. Such short posts 46 allow improved conservation of the trapezium 32, as well as requiring less joint distraction during surgical implantation.

During implantation, the pointed posts are self-aligning and readily received into the softer cancellous interior of the resected trapezium 32. Thus, it is unnecessary to prepare receiving pilot holes in the trapezium 32 for the posts 46. For added stability, the proximal attachment surface 42 can be coated with hydroxylapatite or other osteoconductive material prior to implantation. To further aid fixation, the proximate attachment surface 42 can be roughened or made porous to promote bone ingrowth. However, since the joint is under compressive forces at all times, the posts 46 should be adequate to achieve fixation.

The distal articular surface 44 of the base member 40 includes a convex medial portion 50, a convex lateral portion 52, and a concave central portion 54 between the medial 50 and lateral 52 portions. This complex curvature of the distal articular surface 44 provides stable support to the adjacent first metacarpal 22 throughout the entire arc of thumb circumduction. Further, this unique and advantageous geometry requires little or no alteration of the normal carpometacarpal joint capsular support.

As best shown in FIG. 4, the subject implant 38 includes a perimeter comprising a convex curvature adjacent each of the medial 50 and lateral 52 portions and at least one concave curvature adjacent the central portion 54. In this preferred configuration, the distal articular surface 44 is generally anatomically representative of a natural human trapezium, i.e., one without the degenerative effects of disease or trauma. The perimeter, therefore, comprises a somewhat oval shape having a pronounced jutting end adjacent the lateral portion 52. Therefore, the lateral portion 52 has a greater breadth than the medial portion 50.

The medial portion 50 includes a medial crest 58. Likewise, the lateral portion 52 includes a lateral crest 60 which is of greater length, or elevation, than the medial crest 58. Each of the medial 58 and lateral 60 crests define and establish the convex curvatures of the medial 50 and lateral 52 portions, respectively. Therefore, when placed in operation, the proximal articular surface of the first metacarpal 22 seats within the concave central portion 54 and, during circumduction, reacts along the distal articular surface 44 between the medial crest 58 and the lateral crest 60.

The natural, anatomically correct, curvature of the distal articular surface 44 enhances articulation of the first metacarpal 22 and thereby provides substantially enhanced comfort, as well as reduced likelihood of abrasion. It will be appreciated that because the base member 40 illustrated in FIGS. 2–5 is substantially anatomically representative of a natural trapezium, right and left base members 40 are required due to the differing, mirror-imaged, bones of the trapezium in the natural human hand.

Figure 6:
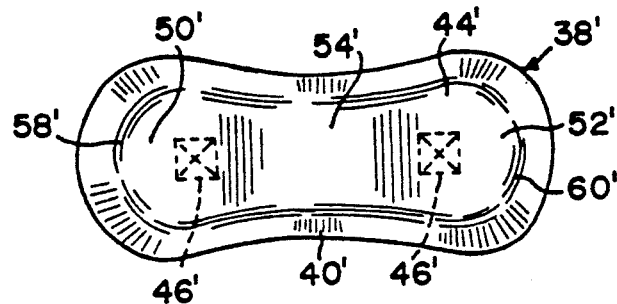
FIG. 6 is a plan view of a first alternative embodiment of the trapezial implant.
Figure 7:
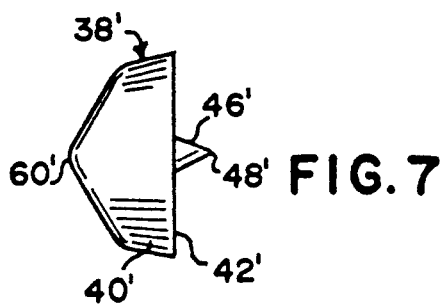
FIG. 7 is a end view of the trapezial implant as in FIG. 6.

According to a first alternative embodiment of the subject invention as shown in FIGS. 6 and 7, the base member 40' can be constructed in a symmetrical fashion, thereby obviating the need for left and right designations. However, symmetry is achieved at the expense of performance, since the anatomically correct implant 38 shown in FIGS. 2–5 has been found through testing to provide superior results. For convenience, single prime designations are used to represent corresponding elements to those described above. The distal articular surface 44' of the implant 38' shown in FIGS. 6 and 7 includes a perimeter having a generally waisted, or hourglass, oval shape. Thus, as shown in the plan view of FIG. 6, the perimeter takes on a somewhat peanut shell shape. Like the previous shape, the medial portion 50' and lateral portion 52' are each convex and are spaced on opposite sides of a concave central portion 54'. Because of the symmetrical nature of the implant 38' of FIGS. 6 and 7, the elevation of the medial 58' and lateral 60' crests must be equivalent.

Figure 8:
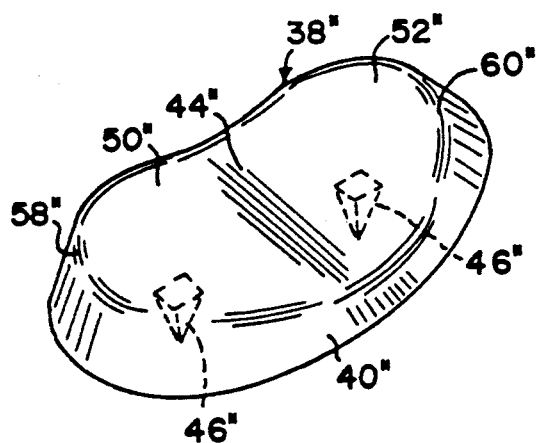
FIG. 8 is a perspective view of a second alternative embodiment of the trapezial implant.
Figure 9:
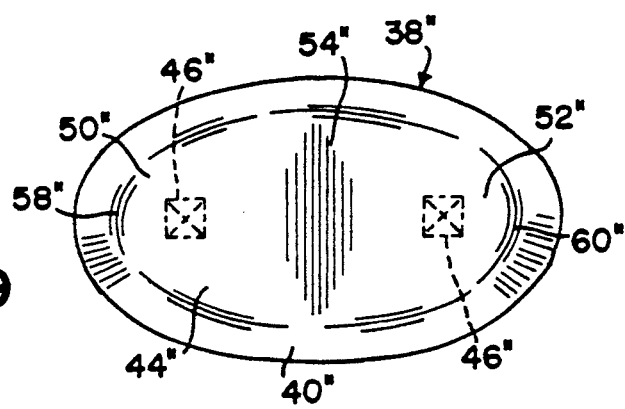
FIG. 9 is a plan view of the trapezial implant as in FIG. 8.
Figure 10:
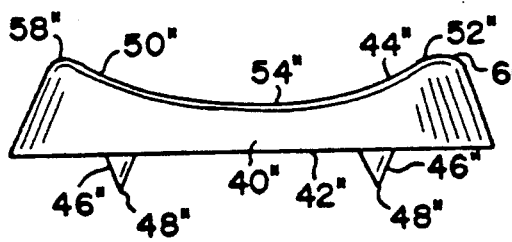
FIG. 10 is a front elevational view of the trapezial implant as in FIG. 9.

A second alternative embodiment of the subject implant 38" is shown in FIGS. 8–10. Double prime designations are used to indicate like or corresponding parts with those discussed above for the sake of convenience. The second alternative implant 38" has a perimeter shape comprising a continuously convex curvature. As best shown by the plan view of FIG. 9, the parameter has a generally ovoid, or elliptical, shape. The distal articular surface 44" provides increased surface area in a concave central portion 54" compared to either of the previous embodiments. And, like the first alternative embodiment of FIGS. 6 and 7, the implant 38" is symmetrical so that left and right designations are not required.

The subject trapezial implant 38, 38', 38" shown in the Figures overcomes the disadvantages of the prior art by means of an anatomically-correct distal articular surface 44 providing stable support to the adjacent first metacarpal 22 throughout the entire arc of thumb circumduction. As a result, fewer wear particles are generated using implants of the invention than obtained with prior art prostheses. This invention permits material selection for the implant 38 to include hard, abrasion-resistant metals, alloys and ceramics rather than softer elastomers. Further, the anchor means is specifically structured to reduce joint distraction during implantation, further allowing improved conservation of the bone of the trapezium 32. Therefore, the subject implant 38 is easier to install than prior art implants.

Although description of the preferred embodiment has focused upon the location of the implant 38 upon the distal trapezium 32, it will be readily appreciated by those skilled in the art that equally successful results can be obtained when the implant 38, or one of the alternative implants 38', 38", is located in other small joints of the body, e.g., the finger or toe joints.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. In a prosthetic device adapted for presenting a prosthetic articular surface on a trapezium in a human hand, said prosthetic articular surface being adapted for engagement with a proximal end of a first metacarpal in said human hand, said prosthetic device including:

(a) a base member defining distal and proximal ends;
(b) said prosthetic articular surface being at said distal end;
(c) an attachment surface at said proximal end; and
(d) anchor means associated with said proximal attachment surface, the improvement comprising, in combination:

(1) said prosthetic device being fabricated from a relatively inelastic, abrasion-resistant and biocompatible material selected from the group consisting of: medical grade metals including titanium, zirconium and alloys thereof; said ceramics including alumina, zirconia and silica;

(2) said prosthetic articular surface having a saddle shaped configuration defined by a convex media portion, a convex lateral portion and a concave central portion therebetween; and an asymmetrical perimeter so as to substantially replicate the articular surface of a human trapezium;

(3) said proximal attachment surface being generally planar;

(4) said anchor means being in the form of a pair of spaced-apart posts extending perpendicularly from said proximal attachment surface and integrally formed with said base;

(5) said posts being tapered and terminating in a point; and (6) said posts having sufficient rigidity to penetrate the cancellous interior of the trapezium without having pilot holes formed in said cancellous interior.

2. In a prosthetic device in accordance with claim 1, the improvement further comprising said attachment surface presenting a roughened or porous surface adapted for promoting bony ingrowth.

* * * * *